United States Patent
Wilczynski et al.

(10) Patent No.: US 9,796,650 B2
(45) Date of Patent: Oct. 24, 2017

(54) INHIBITOR COMBINATION FOR LITHIUM SALT-CATALYZED TRANSESTERIFICATION PROCESS AND METHOD FOR REMOVING LITHIUM SALT

(71) Applicants: Dow Global Technologies LLC, Midland, MI (US); Rohm and Haas Company, Philadelphia, PA (US)

(72) Inventors: Robert Wilczynski, Yardley, PA (US); Christopher R. Eddy, Lake Jackson, TX (US); John O. Osby, Lake Jackson, TX (US); Lan T. P. Hoang Nguyen, Doylestown, PA (US)

(73) Assignees: Dow Global Technologies LLC, Midland, MI (US); Rohn and Haas Company, Philadelphia, PA (US)

( * ) Notice: Subject to any disclaimer, the term of this patent is extended or adjusted under 35 U.S.C. 154(b) by 0 days.

(21) Appl. No.: 15/100,759

(22) PCT Filed: Nov. 21, 2014

(86) PCT No.: PCT/US2014/066745
§ 371 (c)(1),
(2) Date: Jun. 1, 2016

(87) PCT Pub. No.: WO2015/099915
PCT Pub. Date: Jul. 2, 2015

(65) Prior Publication Data
US 2016/0297736 A1 Oct. 13, 2016

Related U.S. Application Data

(60) Provisional application No. 61/920,939, filed on Dec. 26, 2013.

(51) Int. Cl.
| | |
|---|---|
| *C07C 67/03* | (2006.01) |
| *C07C 67/02* | (2006.01) |
| *C08F 2/38* | (2006.01) |
| *C07C 69/587* | (2006.01) |
| *C08F 210/02* | (2006.01) |

(52) U.S. Cl.
CPC ............. *C07C 67/02* (2013.01); *C07C 67/03* (2013.01); *C07C 69/587* (2013.01); *C08F 2/38* (2013.01); *C08F 210/02* (2013.01)

(58) Field of Classification Search
CPC ........ C07C 67/02; C07C 67/03; C07C 69/587
See application file for complete search history.

(56) References Cited

U.S. PATENT DOCUMENTS

| | | | |
|---|---|---|---|
| 3,542,749 A | 11/1970 | Anspon | |
| 4,672,105 A | 6/1987 | Schlosser et al. | |
| 4,916,255 A * | 4/1990 | Kobayashi | C07C 67/03 560/217 |
| 5,072,027 A * | 12/1991 | Kobayashi | C07C 67/03 560/217 |
| 6,048,916 A | 4/2000 | Hirata et al. | |
| 6,509,494 B1 | 1/2003 | Weir | |
| 8,920,885 B2 * | 12/2014 | DeAntoni | C08F 2/48 427/508 |
| 2002/0143120 A1 * | 10/2002 | Yurugi | C07C 67/03 526/89 |
| 2006/0173191 A1 * | 8/2006 | Curtis | C07C 67/03 548/316.4 |
| 2007/0287841 A1 * | 12/2007 | Benderly | B01J 27/10 548/324.1 |
| 2008/0194861 A1 | 8/2008 | Schmitt et al. | |
| 2010/0185009 A1 * | 7/2010 | Schmitt | C07C 67/03 560/225 |
| 2013/0090492 A1 * | 4/2013 | Goossens | B01J 31/2234 558/275 |
| 2013/0237678 A1 | 9/2013 | Osby et al. | |

FOREIGN PATENT DOCUMENTS

| | | |
|---|---|---|
| GB | 1094998 A | 12/1967 |
| JP | H03-106847 A | 5/1991 |
| JP | H03-109350 A | 5/1991 |
| JP | 2002-201159 A | 7/2002 |
| JP | 2007-055910 A | 3/2007 |
| WO | 2013/095969 A1 | 6/2013 |

* cited by examiner

*Primary Examiner* — Vu A Nguyen
(74) *Attorney, Agent, or Firm* — Husch Blackwell LLP

(57) ABSTRACT

A process to form a composition comprising an asymmetrical polyene, the asymmetrical polyene comprising an "α,β unsaturated-carbonyl end" and a "C—C double bond end," the process comprising: reacting an alkene- or polyene-containing alcohol with an alkyl ester of an α,β unsaturated carboxylic acid in the presence of at least the following components A) through C) to form a solution comprising an asymmetrical polyene: A) a lithium salt; B) a component selected from the group consisting of hydroquinone, an alkyl-substituted phenol, a substituted alkyl-substituted phenol, an alkyl-substituted hydroquinone, a substituted alkyl-substituted hydroquinone, and combinations thereof; and C) an N-oxyl-containing compound; wherein the "α,β unsaturated-carbonyl end" of the asymmetrical polyene is selected from the group consisting of structures a) through c), as described herein, and wherein the "C—C double bond end" of the asymmetrical polyene is selected from the group consisting of structures 1) through 17), as described herein.

11 Claims, No Drawings

INHIBITOR COMBINATION FOR LITHIUM SALT-CATALYZED TRANSESTERIFICATION PROCESS AND METHOD FOR REMOVING LITHIUM SALT

BACKGROUND OF THE INVENTION

Lithium hydroxide is a known transesterification catalyst for making methacrylate ester monomers via reaction of methyl methacrylate (MMA) with specialty alcohols (for example, see U.S. Pat. No. 6,048,916, GB 1,094,998, U.S. Pat. No. 5,072,027, U.S. Pat. No. 4,916,255, U.S. Pat. No. 4,672,105, JP 2007055910A). Inhibitors are typically employed in these reactions to keep the monomers from polymerizing during processing. Inhibitors often include, among others, the methyl ether of hydroquinone (MeHQ) and/or phenothiazine (PTZ).

There is continued interest in developing inhibitor combinations which allow the transesterification process to proceed at higher rates while maintaining excellent long term monomer product stability.

When these transesterification reactions are complete, the catalyst is often removed via filtration procedures that include the addition of either some solid filtration agent (such as diatomaceous earth; in addition to above references, also see JP03109350A) or a hydrocarbon solvent (see JP3106847A) to aid in precipitation and/or removal of the precipitated lithium salts. These filtration agents and solvents, however, create more waste and increase disposal costs.

There also remains a need for a process to remove the lithium catalyst (i.e., lithium salt) without the addition of filtration agents or solvents.

SUMMARY OF THE INVENTION

The invention provides a transesterification process to form a composition comprising an asymmetrical polyene, the asymmetrical polyene comprising an "α,β unsaturated carbonyl end" and a "C—C double bond end," the process comprising reacting an alkene- or polyene-containing alcohol with an alkyl ester of an alpha, beta unsaturated carboxylic acid in the presence of at least the following components A) through C), to form a solution comprising the asymmetrical polyene:
  A) a lithium salt;
  B) a component selected from the group consisting of hydroquinone, an alkyl-substituted phenol, a substituted alkyl-substituted phenol, an alkyl-substituted hydroquinone, a substituted alkyl-substituted hydroquinone, and combinations thereof; and
  C) an N-oxyl-containing compound;
wherein the "α,β unsaturated-carbonyl end" of the asymmetrical polyene is selected from the group consisting of structures a) through c), as described herein, and wherein the "C—C double bond end" of the asymmetrical polyene is selected from the group consisting of structures 1) through 17), as described herein.

DETAILED DESCRIPTION OF THE PREFERRED EMBODIMENT

In one embodiment the invention is a process to form a composition comprising an asymmetrical polyene, the asymmetrical polyene comprising an "α,β unsaturated-carbonyl end" and a "C—C double bond end," the process comprising reacting an alkene- or polyene-containing alcohol with an alkyl ester of an α,β unsaturated carboxylic acid in the presence of at least the following components A) through C), to form a solution comprising the asymmetrical polyene:
  A) a lithium salt;
  B) a component selected from the group consisting of hydroquinone, an alkyl-substituted phenol, a substituted alkyl-substituted phenol, an alkyl-substituted hydroquinone, a substituted alkyl-substituted hydroquinone, and combinations thereof; and
  C) an N-oxyl-containing compound;
wherein the "α,β unsaturated-carbonyl end" of the asymmetrical polyene is selected from the group consisting of structures a) through c), as described herein, and wherein the "C—C double bond end" of the asymmetrical polyene is selected from the group consisting of structures 1) through 17), as described herein.

An inventive process may comprise a combination of two or more embodiments described herein.

Alkene- or Polyene-Containing Alcohol

In one embodiment, the transesterification process of the present invention produces an asymmetrical polyene and involves a first step of reacting an alkene- or polyene-containing alcohol with an alkyl ester of an α,β unsaturated carboxylic acid. The term "alkene- or polyene-containing alcohol," as used herein, refers to an organic compound comprising at least one C—C double bond and at least one hydroxyl group.

In one embodiment, the alkene- or polyene-containing alcohol comprises an alcohol selected from the group consisting of the following:

A)
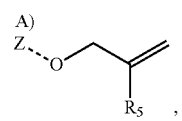

wherein R5 is selected from H or a C1-C6 alkyl;

B)
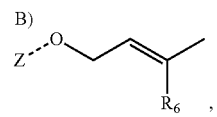

wherein R6 is selected from H or a C1-C6 alkyl;

C)
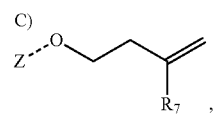

wherein R7 is selected from H or a C1-C6 alkyl;

D)
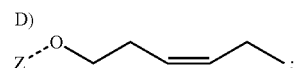

E)
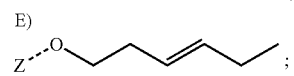

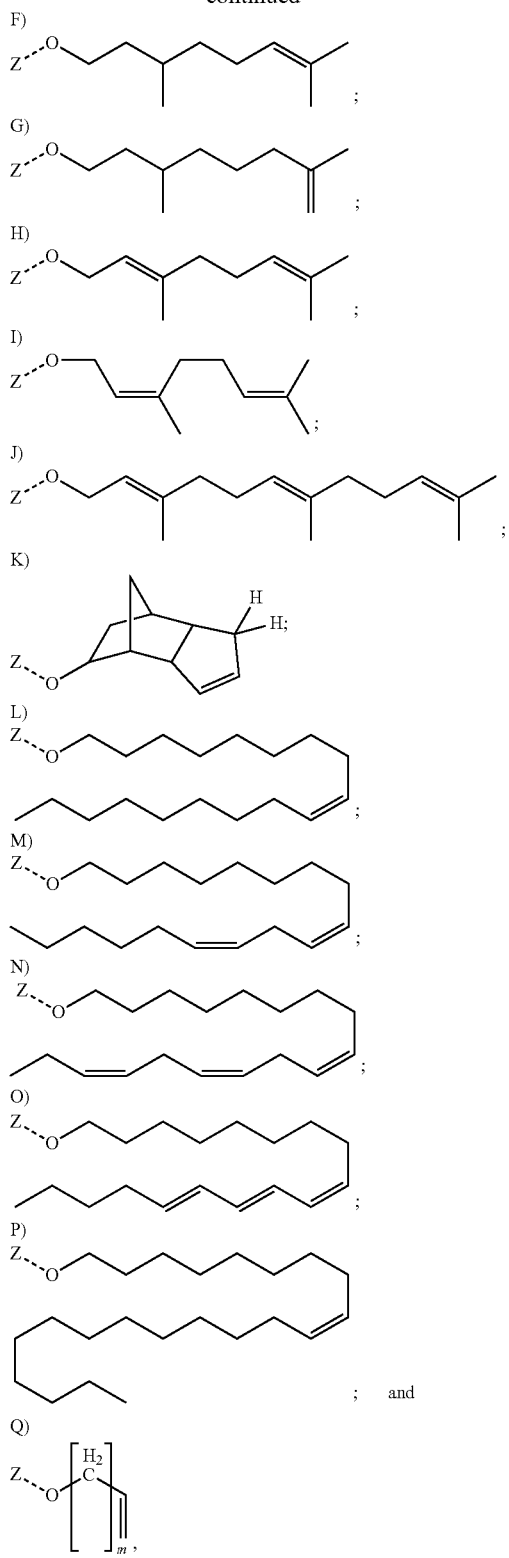

wherein m=1 to 20.

In the structures A) through Q) above, the dashed line (---) represents a bond.

In the structures A) through Q) above, each Z group is independently H or a polyalkylene oxide with the structure:

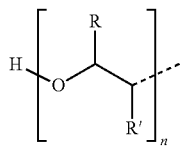

wherein R and R' are independently selected from H, CH$_3$, or CH$_3$CH$_2$, and n is from 0 to 50, and wherein the dashed line (---) represents the connecting bond between the alcohol functionality of the alkene- or polyene-containing alcohol with the polyalkylene oxide moiety.

Peroxides are often present in alkene- or polyene-containing alcohols and their derivatives. These peroxides are undesired because of their propensity to (i) induce unwanted polymer formation from the α,β-unsaturated carboxylates present within the compositions disclosed here, and (ii) produce unwanted byproducts, which can impact downstream applications.

In one embodiment, the alkene- or polyene-containing alcohols used in the present transesterification process preferably have a peroxide level less than 50 ppm, or more preferably less than 20 ppm, or most preferably less than 10 ppm, based on the total weight of the alcohol.

In one embodiment, suitable alkene- or polyene-containing alcohols useful in the present transesterification process include, and are not limited to, polypropylene glycol mono-allyl ether and polyethylene glycol mono-allyl ether.

In one embodiment, the alkene- or polyene-containing alcohol is an alkene-containing alcohol.

In one embodiment, the alkene-containing alcohol is preferably polypropylene glycol allyl ether having the structure:

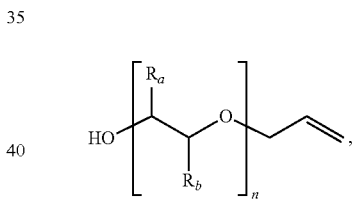

wherein n is 1-20, more preferably 1-15, and even more preferably 1-10; R$_a$ is selected from H or an alkyl (preferably ethyl or methyl, and more preferably methyl); R$_b$ is selected from H or an alkyl (preferably ethyl or methyl, and more preferably methyl); and preferably wherein R$_a$ and R$_b$ are selected from the group consisting of (i) R$_a$ and R$_b$ are both H, (ii) when R$_a$ is methyl, then R$_b$ is H, and (iii) when R$_a$ is H, then R$_b$ is methyl.

Typically, the amount of the alcohol present in the transesterification process described herein is the limiting reactant.

In one embodiment, an alkene- or polyene-containing alcohol may comprise one or more embodiments as described herein. In one embodiment, an alkene- or polyene-containing alcohol may comprise a combination of two or more embodiments as described herein.

Alkyl Ester of an Alpha, Beta-Unsaturated Carboxylic Acid

In one embodiment, the transesterification process of the present invention produces an asymmetrical polyene and involves a first step of reacting an alkene- or polyene-containing alcohol, as described above, with an alkyl ester of an α,β unsaturated carboxylic acid (or α,β unsaturated carboxylic ester). The term "alkyl ester of an α,β unsaturated carboxylic acid," as used herein, refers to an organic compound comprising at least one carbonyl group (CO) and a C—C double bond adjacent to the carbonyl group.

In one embodiment, the alkyl ester of an α,β unsaturated carboxylic acid comprises an alkyl ester of an α,β unsaturated carboxylic acid selected from the group consisting of the following:

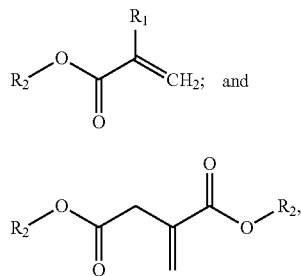

wherein $R_1$ is H or $CH_3$ and each $R_2$ is, independently, a linear or branched $C_1$ to $C_8$ alkyl.

In one embodiment, suitable alkyl esters of α,β unsaturated carboxylic acids useful in the transesterification process of the present disclosure include, and are not limited to, methyl acrylate, methyl methacrylate, ethyl methacrylate, butyl methacrylate, methyl itaconate, ethyl itaconate, and butyl itoconate and combinations thereof.

In one embodiment, the alkyl ester of an α,β unsaturated carboxylic acid is preferably selected from methyl acrylate and methyl methacrylate. In one embodiment, the alkyl ester of an α,β unsaturated carboxylic acid is more preferably methyl methacrylate.

In one embodiment, the alkyl ester of an α,β unsaturated carboxylic acid comprises methyl methacrylate having the structure (III):

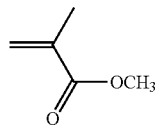

Typically, the amount of alkyl ester of an α,β unsaturated carboxylic acid in the reaction mixture is in stoichiometric excess to the amount of alkene- or polyene-containing alcohol present. In one embodiment, the mole ratio of alkene or polyene-containing alcohol to alkyl ester of an α,β unsaturated carboxylic acid is from 1:1.2 to 1:20.

In a more preferred embodiment, the mole ratio of alkene- or polyene-containing alcohol to alkyl ester of an α,β unsaturated carboxylic acid is from 1:1.12 to 1:10.

In an even more preferred embodiment, the mole ratio of alkene- or polyene-containing alcohol to alkyl ester of an α,β unsaturated carboxylic acid is from 1:2 to 1:6.5

In the most preferred embodiment, the mole ratio of alkene- or polyene-containing alcohol to alkyl ester of an α,β unsaturated carboxylic acid is from 1:2 to 1:5.

In one embodiment, the alkyl ester of an α,β unsaturated carboxylic acid comprises one or more embodiments as described herein. In one embodiment, the alkyl ester of an α,β unsaturated carboxylic acid comprises a combination of two or more embodiments as described herein.

Lithium Sail

In one embodiment, the process of the invention is a transesterification process comprising reacting an alkene- or polyene-containing alcohol with an alkyl ester of an α,β unsaturated carboxylic acid in the presence of at least A) a lithium salt ("component A"); B) a component selected from the group consisting of hydroquinone, an alkyl-substituted phenol, a substituted alkyl-substituted phenol, an alkyl-substituted hydroquinone, a substituted alkyl-substituted hydroquinone, and combinations thereof ("component B"); and C) an N-oxyl-containing compound ("component C").

In one embodiment, the lithium salt (component A) comprises a single lithium salt.

In one embodiment, the lithium salt is a mixture of two or more lithium salts.

In one embodiment, the lithium salt is part of a mixed salt catalyst, such as those known for catalyzing transesterification processes and described in US 2007/028784.

In one embodiment, the lithium salt is selected from the group consisting of lithium salts having the general formula $Li_nX$, wherein n is from 1 to 2 and X is selected from the group consisting of hydroxide, oxide, halide, sulfate, bisulfate, sulfonate, phosphate, phosphonate, perchlorate, nitrate, alkoxide ($RO^-$, wherein R is a straight chain or branched alkyl group having 1 to 8 carbon atoms), phenoxide, carbonate (i.e. $CO_3^{-2}$), bicarbonate (i.e. $HCO_3^-$), alkonate ($RCO_2^-$, wherein R is a straight chain or branched alkyl having 1-8 carbon atoms), alkenoates ($RCO_2^-$ wherein R is an olefin such as —C=C— or —C=C($CH_3$)—), or any other stable anionic moieties capable of forming ionic salts.

In one embodiment, the lithium salt is selected from the group consisting of lithium salts having the general formula $Li_nX$, wherein n is from 1 to 2 and X is selected from the group consisting of hydroxide, oxide, halide, sulfate, bisulfate, sulfonate, phosphate, phosphonate, perchlorate, nitrate, alkoxide ($RO^-$, wherein R is a straight chain or branched alkyl group having 1 to 8 carbon atoms), phenoxide, carbonate (i.e. $CO_3^{-2}$), bicarbonate (i.e. $HCO_3^-$), alkonate ($RCO_2^-$, wherein R is a straight chain or branched alkyl having 1-8 carbon atoms), and alkenoates ($RCO_2^-$ wherein R is an olefin such as —C=C— or —C=C($CH_3$)—).

In one embodiment, the lithium salt is a lithium salt having the general formula $Li_nX$, as described above, and may include the following structures:

$$Li^+_n X^-,$$

wherein n is from 1 to 2, X is selected from the group consisting of $OH^-$, $O^{-2}$, a halide (including, but not limited to, Cl, Br, I, and F), $CO_3^{-2}$, $HCO_3^-$, and $R'CO_2^-$; wherein R is selected from a $C_1$-$C_8$ straight chain or branched alkyl group or from an aryl group; and wherein R' is selected from a $C_1$-$C_8$ straight chain or branched alkyl group, an aryl group, or a $C_1$-$C_3$ alkene group (including, but not limited to, —C=C— or —C=C($CH_3$)—).

In one embodiment, the lithium salt is selected from the group consisting of lithium hydroxide, anhydrous lithium hydroxide, lithium methoxide, lithium carbonate, lithium chloride, lithium acetate, and lithium methacrylate, and combinations thereof.

In one embodiment, the lithium salt preferably comprises anhydrous lithium hydroxide.

In one embodiment, the amount of lithium salt used in the inventive process is from 0.1 to 10 mole %, or more preferably from 0.5 to 5 mole %, or most preferably from 1 to 2 mole %, based on the total moles of alkene- or polyene-containing alcohol in the reaction mixture.

In one embodiment, the lithium salt comprises one or more embodiments described herein.

Typically, lithium salt catalysts, such as those described herein, perform best when water is removed from the reactants prior to starting the transesterification reaction. Low levels of water sometimes found in the starting reactants, such as the alkene- or polyene-containing alcohols and for the alkyl ester of an α,β unsaturated carboxylic acid, can be removed, prior to the addition of the lithium salt by, for example, simple distillation of the reaction mixture until a small amount of the alkyl ester of an α,β unsaturated carboxylic acid is distilled overhead. Typically, less than 5% of the starting alkyl ester of an α,β unsaturated carboxylic acid is removed by distillation from the alcohol/carboxylate mixture. More preferably, less than 3% of the starting alkyl ester of an α,β unsaturated carboxylic acid is removed by distillation. Most preferably, less than 2% of the starting alkyl ester of an α,β unsaturated carboxylic acid is removed by distillation.

In one embodiment, distillation is carried out until water levels within the composition containing the alkene- or polyene-containing alcohol and the alkyl ester of an α,β unsaturated carboxylic acid is less than 0.10%, more preferably less than 0.05%, and most preferably less than 0.03% by weight based on the total weight of the solution including the alkene- or polyene-containing alcohol and alkyl ester of an α,β unsaturated carboxylic acid.

In one embodiment, the water level is most preferably less than 0.03% by weight based on the total weight of the solution including the alkene- or polyene-containing alcohol and alkyl ester of an α,β unsaturated carboxylic acid prior to adding the lithium salt.

Inhibitors

In one embodiment, the alkene- or polyene-containing alcohol and alkyl ester of an α,β unsaturated carboxylic acid are reacted in the presence of at least two inhibitors. Inhibitors prevent the monomers of alkyl ester of an α,β unsaturated carboxylic acid present, including the asymmetrical polyene monomers formed by the inventive process, from polymerizing during transesterification and during storage. Inhibitors may also impact process stability for downstream applications.

In one embodiment, inhibitors include, and are not limited to, oxygen; diethylhydroxylamine; benzoquinone; hydroquinone (HQ); alkyl ethers of hydroquinone and derivatives thereof (including, for example, the methyl ether of hydroquinone (MeHQ) and derivatives thereof); phenothiazine; 2,3-dihydroxylnapthalene; dialkylpara-cresol (including, for example, 2,6-di-t-butylpara-cresol); dialkyl-4-hydroxyanisole (including, for example, 3,5-di-t-butyl-4-hydroxyanisole); dialkylhydroxyanisole (including, for example, 2,5-di-t-butylhydroxyanisole); trialkylphenol (including, for example, 2,4,6-tri-tert-butylphenol); dialkyl-6-alkylphenol (including, for example, 2,4-dimethyl-6-tert-butylphenol (topanol A)); 4-hydroxy-2,2,6,6-tetra-alkyl piperidinyloxy free radical and derivatives thereof (including, for example, 4-hydroxy-2,2,6,6-tetramethyl piperidinyloxy free radical (4-hydroxy-TEMPO or 4-HT) and derivatives thereof); 4-methacryloyloxy-2,2,6,6-tetraalkyl piperidinyloxy free radicals (including, for example, 4-methacryloyloxy-2,2,6,6-tetramethyl piperidinyloxy free radical); and 4-hydroxy-2,2,6,6-tetraalkyl N-hydroxy piperidine (including, for example, 4-hydroxy-2,2,6,6-tetramethyl N-hydroxy piperidine); 2,2,5,5-tetraalkyl-3-oxopyrrolidine-1-oxyl free radical and derivatives thereof (including, for example, 2,2,5,5-tetramethyl-3-oxopyrrolidine-1-oxyl free radical); 2,2,6,6-tetraalkylpiperidine-1-oxyl free radical and derivatives thereof (including, for example, 2,2,6,6-tetramethylpiperidine-1-oxyl free radical); tris(2,2,6,6-tetraalkylpiperidine-1-oxyl-4-yl)-phosphite and derivatives thereof (including, for example, tris(2,2,6,6-tetramethylpiperidine-1-oxyl-4-yl)-phosphite); and mixtures thereof.

In the exemplary inhibitors described above, the alkyl group may be a substituted alkyl or unsubstituted alkyl group.

In one embodiment, the total amount of inhibitor used in the inventive process is at least 100 ppm to at most 3,500 ppm, or more preferably at most 2,500 ppm, or most preferably at most 2,000 ppm, based on the amount in weight of alkene- or polyene-containing alcohol.

In one embodiment, the total amount of inhibitor in the reaction mixture is from 200 to 2,500 ppm based on the amount in weight of alkene- or polyene-containing alcohol.

In one embodiment, a combination of at least two inhibitors is used.

In one embodiment, a combination of at least two inhibitors is used, wherein the first inhibitor is a hydroquinone- or phenol-type inhibitor (including, for example, hydroquinone, alkyl substituted phenol, or alkyl substituted hydroquinone), and wherein the second inhibitor is an N-oxyl-containing compound.

In one embodiment, a combination of at least two inhibitors is used, wherein the first inhibitor (component B) comprises a component selected from the group consisting of hydroquinone, an alkyl-substituted phenol, a substituted alkyl-substituted phenol, an alkyl-substituted hydroquinone, a substituted alkyl-substituted hydroquinone, and combinations thereof, and wherein the second inhibitor (component C) comprises a piperidinyloxy radical-type inhibitor (including piperidinyloxy radicals with an alkyl- or hydroxyl-substitution on the cyclic ring structure).

In one embodiment, a combination of at least two inhibitors is used, wherein the first inhibitor (component B) comprises a component selected from the group consisting of hydroquinone, an alkyl-substituted phenol, an alkyl-substituted hydroquinone, and combinations thereof, and wherein the second inhibitor (component C) comprises a piperidinyloxy radical-type inhibitor (including piperidinyloxy radicals with an alkyl- or hydroxyl-substitution on the cyclic ring structure).

In one embodiment, component B has the general structure (IV)

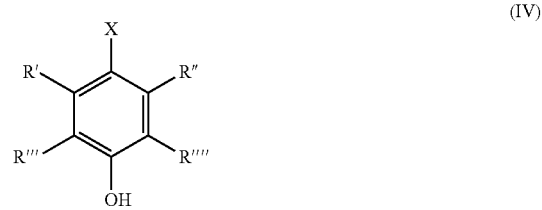

wherein X is R or OR; R is $CH_3$ or H; and each R', R'', R''' and R'''' is, independently, H, a straight chain or branched alkyl group with 1 to 20 carbons, or an aromatic group, including aromatic groups comprising a single aromatic ring or multiple aromatic rings which are fused together, linked covalently, or share a common bond.

In one embodiment, component B is selected from the group consisting of MeHQ, derivatives of MeHQ, and HQ.

In one embodiment, component B is MeHQ or HQ, as shown in structures (V) and (VI), respectively, below.

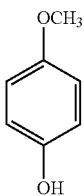

(V)

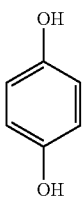

(VI)

In one embodiment, the concentration of component B is from 50 to 3,000 ppm, more preferably from 100 to 2,000 ppm, and most preferably from 250 to 1,500 ppm by weight based on the weight of asymmetrical polyene.

In one embodiment, the second inhibitor comprises an N-oxyl-containing compound (component C). The term "N-oxyl-containing compound," as used herein, refers to any compound and/or chemical substance containing the structural fragment

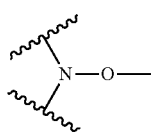 [SMILES: *N(*)OC]

wherein the "·" represents a radical (electron), and each

represents a portion of a covalent bond to a quaternary carbon atom.

In one embodiment, component C (the N-oxyl-containing compound) is selected from the group consisting of 2,2,5,5-tetramethyl-3-oxopyrrolidine-1-oxyl free radical; 2,2,6,6-tetramethylpiperidine-1-oxyl free radical; tris(2,2,6,6-tetramethylpiperidine-1-oxyl-4-yl)-phosphite; and 4-hydroxy-2,2,6,6-tetramethylpiperidine-1-oxyl free radical (4-hydroxy TEMPO, or 4-HT); and derivatives of these compounds.

As used herein, the terms "4-hydroxy-2,2,6,6-tetramethylpiperidine-1-oxyl free radical" and "4-hydroxy-TEMPO" are synonymous and refer to a compound with the structure (VII)

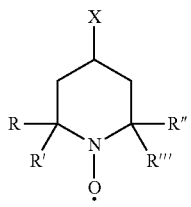

(VIII)

wherein X is H, —OH, or —OR; and each R—R''' is, independently H or an alkyl. In one embodiment, each R—R''' is preferably $CH_3$.

In one embodiment, component C is preferably selected from the group consisting of 4-hydroxy TEMPO and derivatives thereof.

In one embodiment, component C is preferably 4-hydroxy TEMPO.

In an embodiment, the concentration of component C (the N-oxyl-containing compound) used in the process described herein is less than that of component B.

In one embodiment, the concentration of component C is from 50 to 250 ppm, or more preferably from 75 to 125 ppm by weight based on the weight of asymmetrical polyene.

Asymmetrical Polyenes

In one embodiment, the inventive process is a transesterification process to form a composition comprising an asymmetrical polyene which contains an "α,β unsaturated-carbonyl end" and a "C—C double bond end." The asymmetrical polyenes resulting from the process described herein are useful as monomers in further polymerization reactions.

In one embodiment, the "α,β unsaturated-carbonyl end" of the asymmetrical polyene is selected from the group consisting of the following:

a)

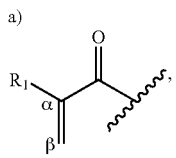

wherein $R_1$ is selected from H or a $C_1$-$C_6$ alkyl (preferably a $C_1$-$C_3$ alkyl and more preferably $CH_3$);

b)

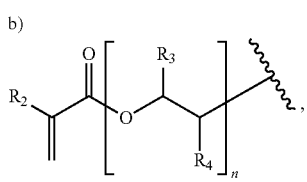

wherein $R_2$ is selected from H or a $C_1$-$C_6$ alkyl (preferably a $C_1$-$C_3$ alkyl and more preferably $CH_3$); $R_3$ is selected from H, $CH_3$, or $CH_2CH_3$; $R_4$ is selected from H, $CH_3$, or $CH_2CH_3$; and n is from 1 to 50, or from 1 to 20, or further from 1 to 10; and c)

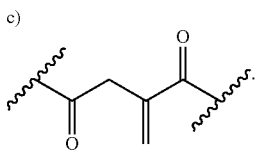 [SMILES: *C(=O)CC(=C)C(*)=O]

In the structures a) through c) above, the notation "〰" represents a break at the center of a covalent bond between the "α,β unsaturated-carbonyl end" of the asymmetrical polyene and the remaining chemical structure of the asymmetrical polyene.

In one embodiment, the "α,β unsaturated-carbonyl end" of the asymmetrical polyene is a) as shown above.

In one embodiment, the "α,β unsaturated-carbonyl end" of the asymmetrical polyene is selected from the group consisting of the following: b) and c), each as shown above, and in a further embodiment, b) wherein $R_3$ and $R_4$ are both H; or when $R_3$ is $CH_3$ or $CH_2CH_3$, then $R_4$ is H; or when $R_4$ is $CH_3$ or $CH_2CH_3$, then $R_3$ is H.

In one embodiment, the "α,β unsaturated-carbonyl end" of the asymmetrical polyene is b) as shown above. In a further embodiment, the "α,β unsaturated-carbonyl end" of the asymmetrical polyene is b) as shown above, and in a further embodiment, b) wherein $R_3$ and $R_4$ are both H, or when $R_3$ is $CH_3$ or $CH_2CH_3$, and $R_4$ is H, or when $R_4$ is $CH_3$ or $CH_2CH_3$, and $R_3$ is H.

In one embodiment, the "α,β unsaturated-carbonyl end" of the asymmetrical polyene is c) as shown above.

In one embodiment, the "C—C double bond end" of the asymmetrical polyene is selected from the group consisting of the following:

1)

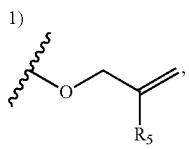

wherein R5 is selected from H or C1-C6 alkyl;

2)

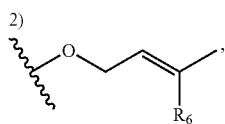

wherein R6 is selected from H or C1-C6 alkyl;

3)

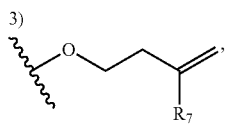

wherein R7 is selected from H or C1-C6 alkyl;

4)

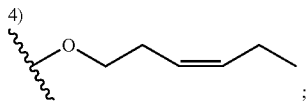

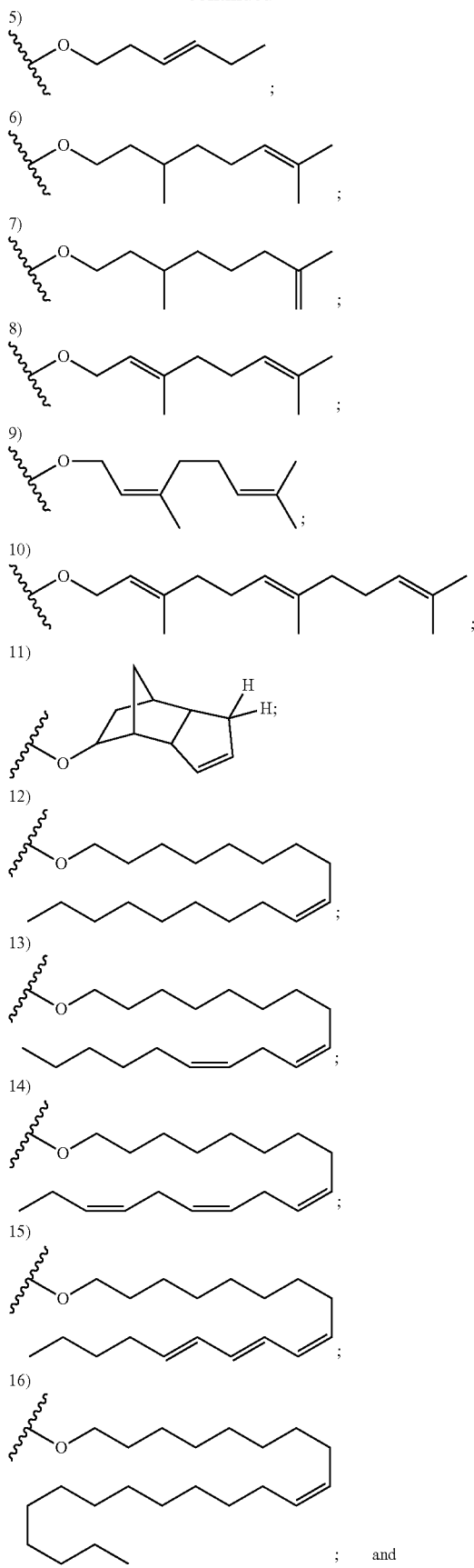

17) 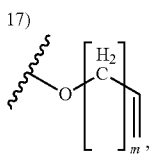

wherein m=1 to 20.

In the structures 1) through 17) above, the "⌇⌇⌇⌇" notation represents a break at the center of a covalent bond between the "C—C double bond end" of the asymmetrical polyene and the remaining chemical structure of the asymmetrical polyene.

In one embodiment, the "C—C double bond end" of the asymmetrical polyene is selected from the group consisting of the following: 1)-15) and 17), each as shown above.

In one embodiment, the "C—C double bond end" of the asymmetrical polyene is selected from the group consisting of the following: 1), 2), 3), 4), 5), 6), 7), 8), 9), 10), 11), 12), and 17), each as shown above.

In one embodiment, the "C—C double bond end" of the asymmetrical polyene is selected from the group consisting of the following: 1), 2), 3), 12), and 17) each as shown above.

In one embodiment, the "C—C double bond end" of the asymmetrical polyene is selected from the group consisting of the following: 13), 14), 15) and 16), each as shown above.

In one embodiment, the asymmetrical polyene is selected from the group consisting of the following:

i) 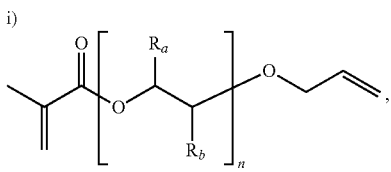

wherein n is from 1 to 50, further from 1 to 20 and further from 1 to 10; $R_a$ is selected from H or an alkyl (preferably ethyl or methyl and more preferably methyl); $R_b$ is selected from H or an alkyl (preferably ethyl or methyl and more preferably methyl); and preferably wherein $R_a$ and $R_b$ are selected from the group consisting of (i) $R_a$ and $R_b$ are both H, (ii) when $R_a$ is methyl, then $R_b$ is H, and (iii) when $R_a$ is H, then $R_b$ is methyl;

ii) 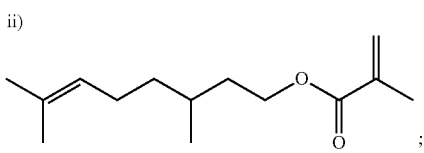

iii) 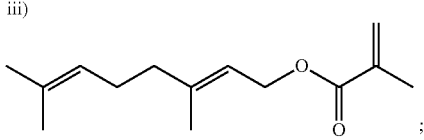

iv) 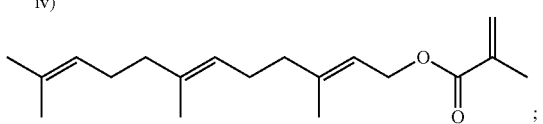

v) 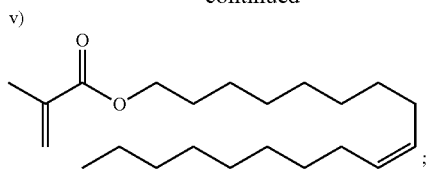

vi) 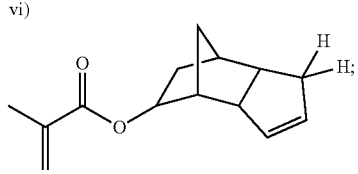

vii) 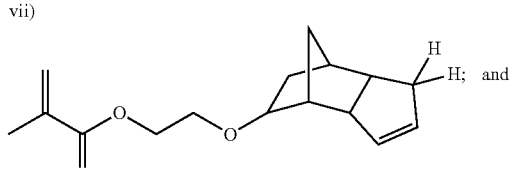

viii) 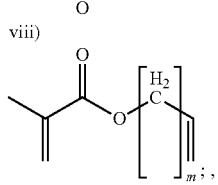

wherein m=1 to 20.

In one embodiment, the asymmetrical polyene is selected from the group consisting of the following: i), ii), iii), iv) and v), each as shown above.

In one embodiment, the asymmetrical polyene is selected from the group consisting of the following: i) and v), each as shown above.

In one embodiment, the asymmetrical polyene is selected from the group consisting of the following: vi), vii), and viii), each as shown above.

In one embodiment, the asymmetrical polyene is polypropylene glycol allyl ether methacrylate (PPG AEMA) having the structure

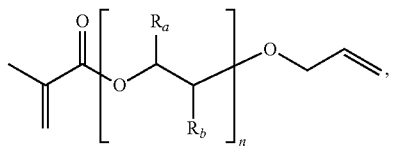

wherein n is from 1 to 50, further from 1 to 20 and further from 1 to 10; $R_a$ is selected from H or an alkyl (preferably ethyl or methyl and more preferably methyl); $R_b$ is selected from H or an alkyl (preferably ethyl or methyl and more preferably methyl); and preferably wherein $R_a$ and $R_b$ are selected from the group consisting of (i) $R_a$ and $R_b$ are both H, (ii) when $R_a$ is methyl, then $R_b$ is H, and (iii) when $R_a$ is H, then $R_b$ is methyl.

Asymmetrical Polyene Composition

In an embodiment, the present invention provides a composition comprising the asymmetrical polyene composition. The composition may include an asymmetrical polyene, inhibitors, and lithium salt.

In one embodiment, the total amount of inhibitor and/or derivative(s) thereof present in the asymmetrical polyene composition is from 75 to 3,500 ppm.

In one embodiment, when a combination of at least two inhibitors (component B and component C) is used, the amount of first inhibitor and/or derivative(s) thereof (component B) present in the asymmetrical polyene composition is from 50 to 3000 ppm based on the weight of the composition, and the amount of the second inhibitor and/or derivative(s) thereof (component C) present in the asymmetrical polyene composition is from 25 to 500 ppm based on the weight of the composition.

In one embodiment, the asymmetrical polyene composition includes an asymmetrical polyene and, preferably, less than 100 ppm of the second inhibitor (component C), which is an N-oxyl-containing compound and/or derivative(s) thereof, wherein the ppm is based on the weight of the asymmetrical polyene.

In one embodiment, the asymmetrical polyene composition includes an asymmetrical polyene and, preferably, from 500 ppm to 1500 ppm of the first inhibitor (component B), and 75 ppm of the second inhibitor (component C), wherein the ppm is based on the weight of the asymmetrical polyene.

In one embodiment, the amount of first and second inhibitor (components B and C) present in the asymmetrical polyene composition is determined by mass balance equation.

In one embodiment, the asymmetrical polyene composition comprise less than 100 ppm of an inhibitor selected from the group consisting of 4-HT, and/or derivatives thereof, and less than 2000 ppm MeHQ and/or derivatives thereof, each based on the weight of the composition. In one embodiment, the amount of 4-HT and/or its derivatives in ppm is determined from a mass balance equation. In one embodiment, the amount of MeHQ and/or derivatives thereof in ppm is determined using HPLC or GC.

In one embodiment, the composition comprises unreacted alkene- or polyene-containing alcohol and/or unreacted alkyl ester of an α,β unsaturated carboxylic acid in addition to asymmetrical polyene, inhibitors, and lithium salt. In one embodiment, the composition comprises from 2% to 10%, or from 2% to 8%, or from 2% to 6%, or from 2% to 4%, by weight, of unreacted alkene- or polyene-containing alcohol, based on the total weight of the composition. In one embodiment, the composition comprises less than 10%, or less than 8%, or less than 6%, or less than 2%, by weight, of unreacted alkene- or polyene-containing alcohol, based on the total weight of the composition. In one embodiment, the composition may include by-products, such as Michael adducts. In one embodiment, the composition comprises from 2% to 10%, or from 2% to 8%, or from 2% to 6%, or from 2% to 4%, by weight, of Michael adducts based on the total weight of the composition. In one embodiment, the composition comprises less than 10%, or less than 8%, or less than 6%, or less than 4%, by weight, of Michael adducts, based on the total weight of the composition.

Applications

In one embodiment, the invention includes an asymmetrical polyene made an inventive process described herein.

In one embodiment, the asymmetrical polyene or asymmetrical polyene composition may be used to form a polymer. In one embodiment, the polymer is an ethylene-based polymer. In one embodiment, the polymer is low density polyethylene (LDPE).

In one embodiment, the polymer, made using the asymmetrical polyene composition, and polymer blends, and/or compositions including the asymmetrical polyene, may be used to form an article or at least one component of an article.

In one embodiment, the polymer made using the asymmetrical polyene composition, and polymer blends, and/or composition including the asymmetrical polyene, may be employed in a variety of conventional thermoplastic fabrication processes to produce useful articles, including extrusion coating onto various substrates; monolayer and multilayer films; molded articles, such as blow molded, injection molded, or rotomolded articles; coatings; fibers; and woven or non-woven fabrics.

In one embodiment, a polymer made using the symmetrical polyene composition, and polymer blends, and/or compositions including the asymmetrical polyene, may be used in a variety of films, including but not limited to, clarity shrink films, collation shrink films, cast stretch films, silage films, stretch hood, sealants, and diaper backsheets.

Other suitable applications include, but are not limited to, wires and cables, gaskets and profiles, adhesives; footwear components, and auto interior parts.

Transesterification Process

In an embodiment, the present invention is a transesterification process to form a composition comprising an asymmetrical polyene which contains an "α,β unsaturated-carbonyl end" and a "C—C double bond end," the process comprising reacting an alkene- or polyene-containing alcohol with an alkyl ester of an α,β unsaturated carboxylic acid in the presence of at least the following components: A) a lithium salt; B) a hydroquinone, alkyl-substituted phenol, or alkyl-substituted hydroquinone; and C) an N-oxyl-containing compound to form a solution comprising the asymmetrical polyene, and wherein the "α,β unsaturated-carbonyl end" of the asymmetrical polyene is selected from the group consisting of structure a)-c), as described herein, and the "C—C double bond end" of the asymmetrical polyene is selected form the group consisting of structures 1)-17), as described herein.

In one embodiment, the alkene- or polyene-containing alcohol, the α,β unsaturated carboxylic ester, lithium salt (component A) and inhibitors (components B and C) may be added to the reaction in any order.

In one embodiment, the alkene- or polyene-containing alcohol, the alkyl ester of an α,β unsaturated carboxylic acid and the inhibitors (components B and C) are first combined, followed by addition of the lithium salt (component A). In another embodiment, the alkyl ester of an α,β unsaturated carboxylic acid and inhibitors (components B and C) are first combined, followed by the addition of the alkene- or polyene-containing alcohol, and, separately, the lithium salt (component A).

In one embodiment, most preferably, the alkene- or polyene-containing alcohol, the alkyl ester of an α,β unsaturated carboxylic acid and the inhibitors (components B and C) are first combined, and the resulting mixture is heated to distill a small amount of the alkyl ester of an α,β unsaturated carboxylic acid overhead to help remove low levels of water which may be present in the raw materials (i.e., alkene- or polyene-containing alcohol, alkyl ester of an α,β unsaturated carboxylic acid and inhibitors). After the dehydration, the lithium salt (component A) is added to the reaction.

In one embodiment, after the alkene- or polyene-containing alcohol, alkyl ester of an α,β unsaturated carboxylic acid, inhibitors (components B and C) and lithium salt (component A) are each added to the reaction, the reaction mixture is heated to above 60° C., and preferably to a reaction temperature which ranges from 70° C. to 140° C., for transesterification to occur.

In one embodiment, the reaction temperature is preferably from 70° C. to 125° C., more preferably from 80° C. to 120° C., or most preferably from 85° C. to 100° C.

In one embodiment, the reaction pressure is typically from 760 mmHg to reduced pressures. Preferably, the reaction pressure is from 250 to 760 mmHg, or more preferably from 400 to 760 mmHg.

In one embodiment, the reaction time is typically from 3 to 48 hours, and preferably from 5 to 18 hours, and most preferably 6 to 12 hours.

In one embodiment, the reactor overhead can possess either a packed or trayed distillation column or other means to help establish an azeotrope between the alkyl ester of an α, β unsaturated carboxylic acid [e.g. (meth)acrylate ester] and the alcohol of reaction, or alcohol2, which is the corresponding alcohol from the ester portion of the alkyl ester of an α,β unsaturated carboxylic acid (for example, methanol would be formed from transesterification reactions involving methyl methacrylate). The azeotrope typically is composed of a higher concentration of the alcohol2 over the (meth)acrylate. In this way, the by-product alcohol2 can be removed with minimum loss of the (meth)acrylate raw material.

Removal of Excess Alkyl Ester of an α,β Unsaturated Carboxylic Acid

In one embodiment, the process of the present invention includes removing excess alkyl ester of an α,β unsaturated carboxylic acid.

In one embodiment, the step of removing excess alkyl ester of an α,β unsaturated carboxylic acid comprises cooling the asymmetrical polyene solution and distilling the alkyl ester of an α,β unsaturated carboxylic acid. In one embodiment, the solution is cooled to below 50° C.

In one embodiment, the alkyl ester of an α,β unsaturated carboxylic acid is distilled using a straight lead distillation tower.

In one embodiment, the distillation rate is maintained such that distillation is complete in 1 to 4 hours, or preferably 1 to 3 hours, or more preferably 1 to 3 hours, or most preferably 1 to 20 hours.

In one embodiment, the step of removing excess alkyl ester of an α,β unsaturated carboxylic acid comprises cooling the asymmetrical polyene solution, preferably to below 50° C., and applying a vacuum to bring the pressure down to less than or equal to 200 mmHg prior to distilling the alkyl ester of an α,β unsaturated carboxylic acid.

In one embodiment, the solution is heated to a temperature of greater than or equal to 70° C. after attaining a pressure of less than or equal to 200 mmHg and prior to distilling the alkyl ester of an α,β unsaturated carboxylic acid.

In one embodiment, in order to obtain a distillation rate such that distillation is complete in 1 to 4 hours, or preferably 1 to 3 hours, or more preferably 1 to 3 hours, or most preferably 1 to 20 hours, the pressure is decreased during distillation while the temperature is increased. In one embodiment, in order to obtain the desired distillation rate, the pressure is decreased over about 1 hour to 30 mmHg and the temperature is increases during that 1 hour to 88° C. to 92° C., or preferably 90° C. If possible, the pressure may be further decreased over an additional 15 to 30 minutes while the temperature is maintained at 88° C. to 92° C., or preferably 90° C.

In one embodiment, excess alkyl ester of an α,β unsaturated carboxylic acid removal is complete when no more alkyl ester of an α,β unsaturated carboxylic acid appears overhead after the asymmetrical polyene solution reaches a pressure of less than or equal to 30 mmHg and a temperature of 90° C. In one embodiment, excess alkyl ester of an α,β unsaturated carboxylic acid removal is complete when the amount of alkyl ester of an α,β unsaturated carboxylic acid in the asymmetrical polyene solution is less than or equal to 0.5 weight percent, or preferably less than 0.5 weight percent, as measured by chromatography.

In one embodiment, excess alkyl ester of an α,β unsaturated carboxylic acid removed is recycled and used in further reaction with alkene- or polyene-containing alcohol to form additional asymmetrical polyene, as described herein.

Lithium Salt Removal

In one embodiment, the process of the present invention includes filtering the asymmetrical polyene solution. Filtering the asymmetrical polyene solution may remove lithium salt (component A) present in the solution.

In one embodiment, the process includes filtering the asymmetrical polyene solution using a 10 micron or less filter, or a 5 micron or less filter, or a 2 micron or less filter, or a 1 micron or less filter.

In one embodiment, the process of the present invention includes cooling the asymmetrical polyene solution.

In one embodiment, the process includes cooling the asymmetrical polyene solution to a temperature of less than or equal to 5° C., or less than or equal to 4° C., or less than or equal to 3° C., or preferably, less than or equal to 2° C.

In an embodiment, the transesterification process of the present invention comprises filtering the asymmetrical polyene solution at a temperature of less than or equal to 5° C., using a 10 micron or less filter, or a 5 micron or less filter, or a 2 micron or less filter, or a 1 micron or less filter.

In one embodiment, after transesterification and/or excess alkyl ester of an α,β unsaturated carboxylic acid removal, the temperature of the asymmetrical polyene solution is decreased to less than or equal to 5° C., to cause the lithium salt to precipitate out of solution before filtration.

In one embodiment, the asymmetrical polyene solution is filtered at a temperature of less than or equal to 5° C., or less than or equal to 4° C., or less than or equal to 3° C., or preferably, less than or equal to 2° C., or preferably less than 0° C., using a 10 micron or less filter, or a 5 micron or less filter, or a 2 micron or less filter, or a 1 micron or less filter.

In one embodiment, the asymmetrical polyene solution is filtered at a temperature of less than or equal to 5° C., or less than or equal to 4° C., or less than or equal to 3° C., or preferably, less than or equal to 2° C.

In one embodiment, and most preferably, the asymmetrical polyene solution is filtered at a temperature of less than or equal to 0° C.

In some embodiments, the asymmetrical polyene solution may be held at the temperature of less than or equal to 5° C., for a period of at least 1 hour, or more preferably at least 2 hours, or most preferably at least 3 hours to allow the lithium salt to precipitate prior to filtering.

Applicants surprisingly and unexpectedly discovered that decreasing the temperature of the asymmetrical polyene solution, following transesterification and/or excess alkyl ester of an α,β unsaturated carboxylic acid removal, to less than or equal to 5° C., and filtering the asymmetrical polyene solution, without the use of other additives or filter aids, at the temperature of less than or equal to 5° C., successfully removed the lithium salt such that no visible haze is observed within the final asymmetrical polyene composition, even after then standing at ambient temperatures for over 180 days.

In one embodiment, filtering the asymmetrical polyene solution at a temperature of less than or equal to 5° C., using 1 micron or smaller filter, also results in an asymmetrical polyene solution, which, upon standing at ambient temperature for up to 24 hours after filtration, or up to 72 hours after filtration, or up to 60 days after filtration, or up to 180 days after filtration showed little to no haze.

Definitions

Unless stated to the contrary, implicit from the context, or customary in the art, all parts and percents are based on weight, and all test methods are current as of the filing date of this disclosure. For purposes of United States patent practice, the contents of any referenced patent, patent application or publication are incorporated by reference, in their entirety (or its equivalent US version is so incorporated by reference), especially with respect to the disclosure of definitions (to the extent not inconsistent with any definitions specifically provided in this disclosure) and general knowledge in the art.

The term "alkyl," as used herein, refers to a saturated linear, cyclic, or branched hydrocarbon group. Nonlimiting examples of suitable alkyl groups include, for example, methyl, ethyl, n-propyl, i-propyl, n-butyl, t-butyl, i-butyl (or 2-methylpropyl), etc. In one embodiment, the alkyls have 1 to 20 carbon atoms.

The term "substituted alkyl," as used herein, refers to an alkyl as previously described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, 2-propenyl (or allyl), vinyl, haloalkyl, hydroxy, amino, phosphido, alkoxy, amino, thio, nitro, unsaturated hydrocarbon, and combinations thereof. Suitable substituted alkyls include, for example, benzyl, trifluoromethyl and the like.

The term "composition," as used herein, includes a mixture of materials which comprise the composition, as well as reaction products and decomposition products formed from the materials of the composition.

"Comprising", "including", "having" and like terms are not intended to exclude the presence of any additional component, step or procedure, whether or not the same is specifically disclosed. In order to avoid any doubt, all processes claimed through use of the term "comprising" may include one or more additional steps, pieces of equipment or component parts, and/or materials unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or," unless stated otherwise, refers to the listed members individually as well as in any combination.

The term "polymer" refers to a compound prepared by polymerizing monomers, whether of the same or a different type. The generic term polymer thus embraces the term homopolymer (which refers to polymers prepared from only one type of monomer with the understanding that trace amounts of impurities can be incorporated into the polymer structure), and the term "interpolymer" as defined below. Trace amounts of impurities may be incorporated into and/or within the polymer.

The term "interpolymer" refers to polymers prepared by the polymerization of at least two different types of monomers. The generic term interpolymer includes copolymers (which refers to polymers prepared from two different monomers), and polymers prepared from more than two different types of monomers.

The term "blend," as used herein, refers to a mixture of two or more components.

As used herein, the term "polyene" refers to a poly-unsaturated compound having two or more carbon-carbon double bonds.

The term "ethylene-based polymer" refers to a polymer that comprises a majority amount of polymerized ethylene, based on the weight of the polymer, and, optionally, at least one comonomer.

As used herein, the terms "R1," "R2," and the like, are used interchangeably with "$R_1$," "$R_2$," and the like to refer to corresponding R groups forming part of a chemical structure. Similarly, the terms "C1," "C2," and the like, are used interchangeably with "$C_1$," "$C_2$," and the like to refer to 1- or 2-carbon groups, respectively.

Test Methods

Polymer observation during/after reaction: Polymer observation is determined both by direct observation of reaction and product samples, and also via solvent dilution tests, followed by visual confirmation for lack of haze, solids, gels, coagulum, stringy material, etc. For the solvent dilution tests, samples are tested using both methanol and hexane. To prepare the samples, the reaction mixture is evaluated at various stages, by mixing 1 gram of reaction mixture or final product with 49 grams of anhydrous methanol, for the methanol dilution test, or 49 grams of hexane, for the hexane dilution test. Significant haze development upon dilution, after 5 minutes, using either dilution test, indicates formed polymer and a failed test. Extended storage stability tests are run directly, by placing the monomer at 54° C., and the monomer samples need to last 60 days, without evidence of polymer formation via these test methods. This would qualify the monomer for acceptable storage times during commercial use.

Mass balance is employed for the determination of inhibitor concentration.

Inhibitor concentrations may also be determined by HPLC methods, as well as other methods known in the art.

EXPERIMENTAL

Example 1

Reaction Preparation

A four-necked, 2-liter flask is equipped with a mechanical stirrer, a sparge tube for 8% oxygen in nitrogen gas feed, and a 10-15 sieve-tray distillation column (or packed column), with a condenser on top leading distillate, to a reflux splitter that controls the amount of distillate going forward to a receiver, versus back to the column as reflux; where the receiver leads to a vacuum source that is controlled by a pressure transducer. Thermocouples are placed, within the reactor flask and in the overhead space above the column, to help monitor and control temperatures at these locations. The reaction flask is charged with 400 grams of polypropyleneglycol mono-allyl ether (2 moles), 1000 grams of methyl methacrylate (MMA) (10 moles), and 0.8 grams of the methyl ether of hydroquinone (MeHQ) and then sealed. In Example 2, 0.04 grams of 4-hydroxy-TEMPO (4H-TEMPO) is also added. In addition, 0.2 grams of MeHQ are added to the overhead receiver to inhibit MMA monomer that will collect there. Chilled water (10° C.) is fed to the coolant side of the overhead condenser. The mechanical agitator is turned on and set to 100 rpm. The 8% oxygen in the nitrogen sparge flow is started and maintained at a flow rate of approximately 10 mls/minute.

Dehydration [Prior to Adding the Lithium Salt]:

Vacuum is then applied until the overhead pressure equals 550 mmHg. Once this pressure is attained, the reaction flask is heated via a heating mantle, until the reaction mixture attains a temperature of from 96° C. to 100° C. Under these conditions, distillate fills the column (without flooding the column trays) and is set to reflux completely back to the column. The overhead temperature is monitored, establishing a distillate temperature of from 88° C. to 92° C. Once these conditions are attained, the distillate is taken forward at a 10:1 ratio of reflux:distillate, using the reflux splitter to control this ratio. In this manner, approximately from 2% to 3% of the MMA charge is taken overhead into the receiver. At this point, the distillate is set back to full reflux mode via the reflux splitter, while the water level is checked within the reaction mixture. If the water level is greater than 0.03 weight %, then the distillation is continued, as before, until another 1% to 2% MMA is taken overhead, and the water level is again checked in the batch. Once the water level in the reaction mixture is below 0.03 weight %, then the batch is cooled to the 40° C. to 60° C. range for charging the anhydrous LiOH.

Transesterification

Once the batch is cooled to the 40° C. to 60° C. range, and the pressure is raised to atmospheric, then 0.96 grams (0.04 moles) of anhydrous LiOH is added to the batch, and the reactor is re-sealed. While still applying a sparge rate of about 10 ml/min and a stirrer rate of 100 rpm, vacuum is again applied until the overhead pressure reads 550 mmHg. Once this pressure is attained, the reactor is again heated toward and maintained at 96° C. to 100° C., to fill the column with distillate without flooding the column trays. Full reflux is maintained, as the overhead temperature drops from about 80° C. to approximately 56° C. to 58° C., over a 1 to 2 hour period. This temperature drop in the overhead results from the establishment of an MMA/methanol azeotrope that forms, which is important to maintain during the course of the reaction for faster methanol removal with minimum MMA loss. While the 56° C. to 58° C. overhead temperature is maintained, the distillate is taken forward at a rate of 2.3:1 reflux:distillate ratio. As the overhead temperature later rises above 60° C., the overhead should then be set to full reflux mode, until the overhead temperature comes back down into the 56-58° C. range. Once this is accomplished, the overhead can be reset to the 2.3:1 reflux ratio once more. Overall, the time for this step is approximately 4 to 8 hours, and can be monitored either by measuring the amount of methanol formed in the distillate, or by measuring conversion of the starting alcohol to the corresponding methacrylate ester in the pot using either GC or NMR analysis. Once the analytical confirms that the conversion of the starting alcohol to the ester product is over 97%, the batch will then be stripped of excess MMA.

For some combinations of inhibitor with the lithium salt LiOH, the rate of transesterification is slower, and, at times, an extra shot of LiOH is needed to complete the reaction. This is noted by the loss of the azeotrope in the overhead (i.e., temperature will not drop to the target 56° C. to 58° C. range) along with conversion not reaching >97% in the batch. In these instances, an additional 0.24 grams (0.01 mole) of LiOH is added to the batch to aid in further conversion. This action typically leads to continued removal of azeotrope as described above.

Removal of Excess MMA

Once the alcohol conversion is over 97%, the batch is cooled to below 50° C., and the overhead column is replaced with a straight lead distillation tower. Earlier conditions are maintained for 8% oxygen in nitrogen gas flow, agitator speed, and condenser temperature. Vacuum is applied to bring the overhead pressure down to less than or equal to 200 mmHg. Once this pressure is attained, the batch is heated to 70° C. to begin distilling MMA. A good distillation rate is maintained by reducing the system pressure and increasing the batch temperature gradually. The distillation rate is maintained such that the distillation is complete within 1 to 4 hours, more preferably 1 to 3 hours, most preferably 1 to 2 hours. To accomplish this, the pressure is decreased, over about one hour, to 30 mmHg, while also increasing temperature over this time to 90° C. If possible to lower the pressure further, this should be accomplished over an additional 15 to 30 minutes, while maintaining a batch temperature of 88° C. to 92° C. When no more MMA appears to be coming overhead, after reaching less than 30 mmHg and 90° C. in the batch, a sample is withdrawn from the reaction mixture to measure for residual MMA by chromatography. Once the MMA is below 0.5 weight %, the vacuum is broken with air, and the batch is cooled to ambient temperature. If the MMA level is above 0.5 weight %, then the batch is further held at less than 30 mmHg and also 90° C., for another hour, before checking the MMA level again.

Lithium Salt Removal

Once the batch begins cooling, after the MMA strip step, the temperature of the batch is brought down to 0° C. to 5° C. At this temperature, nearly all of the lithium salt precipitates from the batch. While maintaining the temperature at 0° C. to 5° C., the batch is filtered through a 1 micron sized filter. This gives a clear PPG AEMA monomer product that is light yellow to light brown in color. Total weight of the monomer is 533 grams for a 99.5% yield of liquid product that is over 95% pure.

Examples 2 to 5

Examples 2 to 5 are prepared as described above, except different inhibitors were employed in the various examples as detailed in Table 1.

Table 1 illustrates the beneficial effect of certain inhibitors on conversion versus time, and also on reaction and product stability. The inhibitor amounts listed in Table 1 are based on the starting mixture once all charges of all raw materials are made. Polymer observation is conducted using both methanol and hexane dilution tests.

TABLE 1

Effect of Inhibitors on Conversion v. Time

| Ex. No. | MeHQ[1] (ppm) | 4H-TEMPO[2] (ppm) | PTZ[3] (ppm) | DEHA[4] (ppm) | Time to >97% Conversion | 2$^{nd}$ Shot LiOH?[5] | Polymer Observed after Rx? | Polymer Observed during Extended Storage Time? |
|---|---|---|---|---|---|---|---|---|
| 1 | 590 | 0 | 0 | 0 | 10 hours | Yes | No | Yes |
| 2 | 590 | 28 | 0 | 0 | 4 hours | No | No | No |
| 3 | 590 | 0 | 400 | 0 | 12 hours | Yes | No | No |
| 4 | 590 | 0 | 30 | 0 | Polymer formed after 7 hours | — | Yes | NA |
| 5 | 590 | 0 | 0 | 164 | Polymer formed after 1 hour | — | Yes | NA |

[1]MeHQ = methyl ether of hydroquinone
[2]4H-TEMPO = 4-hydroxy-2,2,6,6-tetramethylpiperidine-1-oxy radical
[3]PTZ = phenothiazine
[4]DEHA = diethylhydroxylamine
[5]The 2$^{nd}$ shot of LiOH is equal to ¼ of the original amount of LiOH added to the batch.

As demonstrated in Table 1, certain combinations of inhibitors result in more stable monomer products. For experiments 2 and 3, using MeHQ as a primary inhibitor (component B), with some amount of 4H-TEMPO or PTZ as a secondary inhibitor (component C), resulted in a monomer product exhibiting no evidence of polymerization, both immediately following the transesterification reaction and after extended storage. Notably, Applicants surprisingly and unexpectedly discovered that the inhibitor combination of MeHQ and 4H-TEMPO not only resulted in a stable product, but also showed decreased reaction time (i.e., 4 hours to reach >97% conversion) compared to using MeHQ alone (i.e. 10 hours to reach >97% conversion) and using MeHQ with PTZ (i.e. 12 hours to reach >97% conversion).

Examples 6 to 11

Examples 6 to 11 are prepared as described according to the general procedure above, except that 0.8 grams of the methyl ether of hydroquinone (MeHQ) and 0.04 grams of 4-hydroxy-TEMPO (4H-TEMPO) are employed as inhibitors for each of examples 6 to 11 and different precipitation and filtration temperatures are used as outlined in Table 2.

Table 2 shows the beneficial effect of lower temperatures on lithium salt removal.

TABLE 2

Effect of Precipitation/Filtration Temperature on Lithium Salt Removal

| Ex. No. | Filtration Temperature (° C.) | Appearance upon Filtration | Appearance 30 minutes after Filtration | Appearance 24 hours after Filtration | Appearance 72 hours after Filtration | Appearance 60 days after Filtration |
|---|---|---|---|---|---|---|
| 6 | 20 | Slight haze | Hazy | Hazy | Hazy | Hazy |
| 7 | 15 | Clear | Hazy | Hazy | Hazy | Hazy |
| 8 | 10 | Clear | Clear | Hazy | Hazy | Hazy |
| 9 | 5 | Clear | Clear | Clear | Hazy | Hazy |
| 10 | 2 | Clear | Clear | Clear | Clear | Clear |
| 11 | 0 | Clear | Clear | Clear | Clear | Clear |

[1]After 3 days, the precipitate that causes haze collects at the bottom of the container. After 60 days of standing, the samples appear clear with solids collected on the bottom of the container. However, once the samples are shaken, they again become hazy. The designation of "hazy" for storage times of 60 days is therefore after shaking.

As demonstrated in Table 2, only those experiments filtered at a temperature of less than or equal to 5° C. resulted in a final monomer composition that remained clear and free of haze for more than 24 hours. Those examples filtered at a temperature of less than or equal to 2° C. remained clear and free of haze for over 6 months. By lowing the filtration temperature to less than, or equal to, 5° C., or less than, or equal to, 2° C., it was possible to remove the lithium salt to an acceptable level, without requiring additives and/or filtration aids. Elimination of these additives results in lower costs for disposal and more environmentally friendly procedures (i.e., less waste). In contrast, all solutions filtered at temperatures greater than 5° C. showed evidence of haze after relatively short times (i.e., within 24 hours).

Examples 12 to 20—Low Density Polyene Batch Reactor Process Stability Studies

Conventional low density polyethylene (LDPE) has good processability; however, when used in film and/or extrusion coating application, increased melt strength is still desired. It has been discovered that such polymers can be produced using asymmetrical polyenes, such as those described herein. However, there is a need to produce such polymers under polymerization conditions with good reactor stability.

It is well known in the industry that under sufficiently high pressures and temperatures or in the presence of an ignition source, ethylene can decompose into carbon, methane and hydrogen. The following mechanism is described by Zimmermann T. and Luft G. in "Explosive decomposition of compressed ethylene", Chemie Ingenieur Technik (1994), 66 (10), 1386-1389:

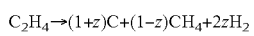

$$C_2H_4 \rightarrow (1+z)C + (1-z)CH_4 + 2zH_2$$

wherein z is in the range from 0 to 1, and depends on the pressure and temperature. This results in a runaway reaction, which results in very high temperatures and pressures which could then lead to equipment damage. Decomposition of ethylene has been studied extensively by Luft and others, as reported in "Safety engineering studies on the explosive decomposition of compressed ethylene", Chemie Ingenieur Technik (1995), 67 (7), 862-864, "Thermal decomposition of Ethylene-comonomer mixtures under high pressure" AIChE Journal (1999), 45 (10), 2214-2222, and "Effect of reactor contamination on highly compressed ethylene" Chemie Ingenieur Technik (2000), 72(12), 1538-1541. Zhang et al. have also described the phenomena in "Runaway phenomena in low-density polyethylene autoclave reactors" AIChE Journal (1996), 42 (10), 2911-2925.

Every new compound introduced in LDPE manufacturing technology which can provide additional radicals over those from peroxides, and therefore provide the temperature needed for the runaway reaction, represented by the above mechanism, is ideally tested for decomposition sensitivity. The propensity for each compound to shift the baseline level of radicals in the process must be considered. In some cases, a given compound may generate radicals independent of other materials injected into the reactor. In other cases, an interaction between two compounds may generate additional radicals.

For the LDPE batch reactor process stability studies, the set-up described by Alberts et al., "Thermal decomposition of Ethylene-comonomer mixtures under high pressure" AIChE Journal (1999), 45 (10), 2214-2222, is used. This set-up is designed for the study of reaction runaways. The volume of the autoclave reactor (or cell) is 215 ml. The wall temperature is controlled by electric heating outside the cell to achieve a starting temperature of 250° C. for the experiments. The cell is designed without an agitator to prevent any damage to the motor due to the high temperature and pressures generated during the runaway reaction. The absence of the mixing and the batch mode of operation are believed to provide a more conservative (extreme case) representation of the behavior in a low density polyethylene tubular reactor.

The following procedure is applied to test the reaction runaway potential of the various stability experiments: (1) the autoclave is purged with ethylene and heated to the starting temperature; (2) the autoclave is pressurized with ethylene to about 1400 bar; (3) ditertiarybutyl peroxide (DTBP) and enough propylene glycol allyl ether methacrylate (PPGAEM) to achieve 100 mol ppm in ethylene once injected into the reactor are mixed together in a feed vessel and then purged with nitrogen to remove oxygen; (4) if necessary, heptane is added as a solvent to ensure the injected volume in all cases is 1 ml; (5) the mixture is added into injection tubing at the entrance to the reactor; and (5) ethylene is allowed to flow into the reactor to push the contents of the injection tubing into the reactor and to pressurize the reactor up to 1900 bar.

Table 3 shows the corresponding amount of DTBP and 4-HT used for the experiment, as well as the amount of active oxygen due to peroxides in the base alcohol (the alcohol used to produce the PPGAEM). The amount of 4-HT in ethylene was based on the weight fraction of 4-HT in the PPGAEM determined from the mass balance when producing the PPGAEM. The temperature of the reactor 30 seconds after injection of the reaction components (T@ 30 s) was recorded, and the results are included for each experiment.

Experiments 12 to 15 illustrate that T@ 30 s rises as the amount of 4-HT is increased when using the same amount of DTBP. Experiment 16 and Experiment 17 illustrate at the same concentration of DTBP, the T@ 30 s was lower for the experiment with the PPGAEM produced from the base alcohol which had a much lower amount of active oxygen due to peroxides. Examples 16 to 20 illustrate it was possible to use higher amounts of DTBP for the experiments with the PPGAEM produced from the base alcohol, which had a much lower amount of active oxygen due to peroxides. As a whole, Experiments 12 to 20 illustrate an improved capability to avoid reactive runaway decomposition reactions through a higher degree of control over radicals or compounds, which can initiate polymerization of ethylene in the high pressure low density polymerization process, when minimizing the 4-HT and the peroxides in the base alcohol used to produce the PPGAEM.

TABLE 3

Low Density Polyethylene Batch Reactor Process Stability Studies

| Ex. No. | Mol ppm PPGAEM in Ethylene | Weight ppm 4-HT in Ethylene | Peroxide in Base Alcohol (active oxygen ppm by weight) | T @ 30 s (° C.) | Mol ppm DTBP in Ethylene |
|---|---|---|---|---|---|
| 12 | 100 | 0 | 1000 | 290 | 2 |
| 13 | 100 | 457 | 1000 | 300 | 2 |
| 14 | 100 | 75 | 1000 | 296 | 2 |
| 15 | 100 | 75 | 1000 | 296 | 2 |
| 16 | 100 | 75 | 1000 | 299 | 2.2 |
| 17 | 100 | 75 | 1000 | 309 | 2.3 |
| 18 | 100 | 72 | 4 | 297 | 2.3 |
| 19 | 100 | 72 | 4 | 297 | 2.4 |
| 20 | 100 | 72 | 4 | 308 | 2.6 |

The invention claimed is:

1. A process to form a composition comprising an asymmetrical polyene, the asymmetrical polyene comprising an "α,β unsaturated-carbonyl end" and a "C—C double bond end," the process comprising:

reacting an alkene- or polyene-containing alcohol with an alkyl ester of an α,β unsaturated carboxylic acid in the presence of at least the following components A) through C) to form a solution comprising the asymmetrical polyene:

A) a lithium salt;

B) a component selected from the group consisting of hydroquinone, an alkyl-substituted phenol, a substituted alkyl-substituted phenol, an alkyl-substituted hydroquinone, a substituted alkyl-substituted hydroquinone, and combinations thereof; and C) an N-oxyl-containing compound;

wherein the "α,β unsaturated-carbonyl end" of the asymmetrical polyene is selected from the group consisting of the following:

a)

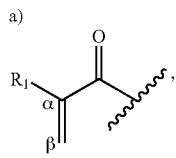

wherein R₁ is selected from H or a C₁-C₆ alkyl;

b)

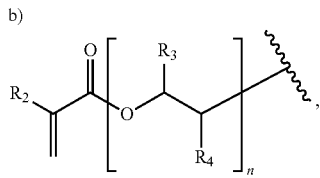

wherein R₂ is selected from H or a C₁-C₆ alkyl; R₃ is selected from H, CH₃, or CH₂CH₃; R₄ is selected from H, CH₃, or CH₂CH₃; and n is from 1 to 50; and c)

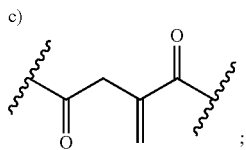 [SMILES: *C(=O)CC(=C)C(*)=O]

and
wherein the "C—C double bond end" of the asymmetrical polyene is selected from the group consisting of the following:

1)

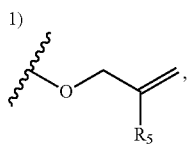

wherein R5 is selected from H or C1-C6 alkyl;

2)

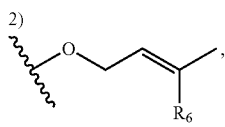

wherein R6 is selected from H or C1-C6 alkyl;

3)

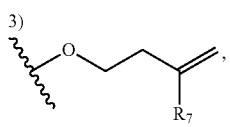

wherein R7 is selected from H or C1-C6 alkyl;

4)

5)

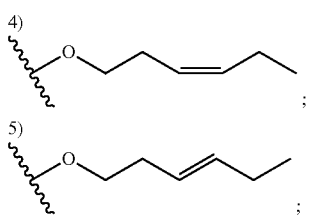

6)

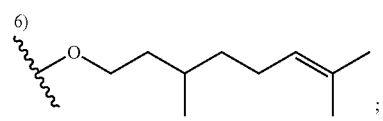

7)

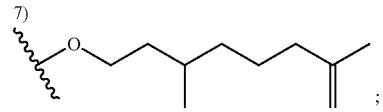

8)

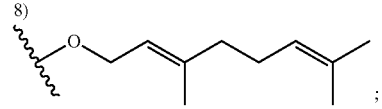

9)

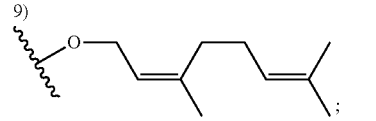

10)

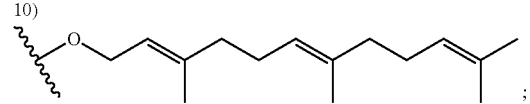

11)

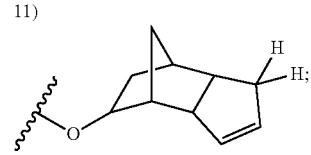

12)

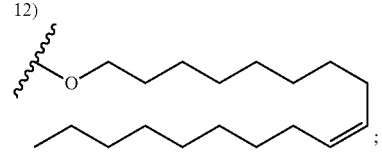

13)

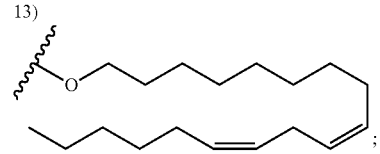

14)

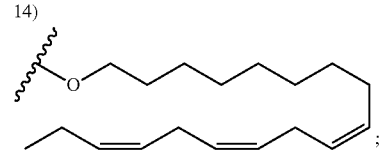

15)

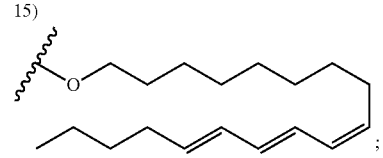

16)

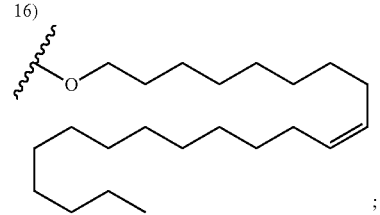

; and

17) 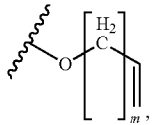

wherein m=1 to 20.

2. The process of claim 1, wherein the lithium salt has the structure $Li_nX$, wherein n is 1 or 2; and X is selected from the group consisting of hydroxide, oxide, halide, carbonate, bicarbonate, alkoxide, alkonate, alkenoate, phenoxide, sulfate, bisulfate, sulfonate, phosphate, phosphonate, perchlorate, and nitrate.

3. The process of claim 1, wherein component A) has the structure $Li_nX$, wherein n is 1 or 2; and X is selected from the group consisting of $OH^-$, $O^{-2}$, a halide, $OR^-$, $CO_3^{-2}$, $HCO_3^-$, and $R'CO_2^-$; wherein R is selected from a C1-C8 straight chain or branched alkyl group or from an aryl group; wherein R' is selected from either a C1-C8 straight chain or branched alkyl group, or an aryl group, or a C1-C3 alkene group.

4. The process of claim 1, wherein component B) is selected from the group consisting of MeHQ, derivatives thereof, and HQ.

5. The process of claim 1, wherein component C) is selected from 4-HT or a derivative thereof.

6. The process of claim 1, wherein the alkyl ester of the α,β unsaturated carboxylic acid is methyl methacrylate.

7. The process of claim 1, wherein the alkene- or polyene-containing alcohol is polypropylene glycol allyl ether.

8. The process of claim 1, wherein the asymmetrical polyene is a polypropylene glycol allyl ether methacrylate.

9. The process of claim 1, wherein component A) is anhydrous lithium hydroxide.

10. The process of claim 1, further comprising the step of filtering the solution comprising the asymmetrical polyene at a temperature of less than or equal to 5° C., using a 10 micron or less filter.

11. The process of claim 10, wherein the solution comprising the asymmetrical polyene is filtered at a temperature of less than or equal to 2° C.

* * * * *